(12) United States Patent
Ekwall

(10) Patent No.: US 6,584,351 B1
(45) Date of Patent: Jun. 24, 2003

(54) IMPLANTABLE CARDIAC STIMULATOR WITH CIRCUITRY FOR REMOVING NOISE IN SENSED ELECTRICAL SIGNALS

(75) Inventor: Christer Ekwall, Spånga (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/600,733

(22) PCT Filed: Jan. 7, 1999

(86) PCT No.: PCT/SE99/00008

§ 371 (c)(1),
(2), (4) Date: Jul. 20, 2000

(87) PCT Pub. No.: WO99/36125

PCT Pub. Date: Jul. 22, 1999

(30) Foreign Application Priority Data

Jan. 2, 1998 (SE) .............................................. 9800126

(51) Int. Cl.$^7$ ................................................. A61N 1/18
(52) U.S. Cl. ........................................... 607/9; 128/901
(58) Field of Search .............................. 128/901; 607/1, 607/2, 9, 27, 36, 62

(56) References Cited

U.S. PATENT DOCUMENTS

| | | | | |
|---|---|---|---|---|
| 4,091,818 A | * | 5/1978 | Brownlee et al. | ............... 607/9 |
| 5,313,953 A | * | 5/1994 | Yomtov et al. | ............. 600/508 |
| 5,331,966 A | * | 7/1994 | Bennett et al. | ............. 600/508 |
| 5,511,553 A | * | 4/1996 | Segalowitz | ................. 600/508 |
| 5,522,860 A | * | 6/1996 | Molin | ............................ 607/9 |
| 5,697,958 A | * | 12/1997 | Paul et al. | ................... 128/901 |
| 6,412,490 B1 | * | 7/2002 | Lee | ............................. 128/897 |

* cited by examiner

Primary Examiner—George R. Evanisko
Assistant Examiner—Omar Khan
(74) Attorney, Agent, or Firm—Schiff Hardin & Waite

(57) ABSTRACT

An implantable medical device, such as a cardiac stimulator, has a noise cancelling circuit which cancels noise signals relating to body movements which originate outside of the heart, and which are sensed between a noise sensing electrode located outside of the heart and the indifferent electrode of the stimulator housing. The noise cancelling circuit cancels these noise signals from the electrical signals which originate within the heart and which are sensed between the tip electrode of a stimulator lead and the indifferent electrode of the stimulator housing.

7 Claims, 3 Drawing Sheets

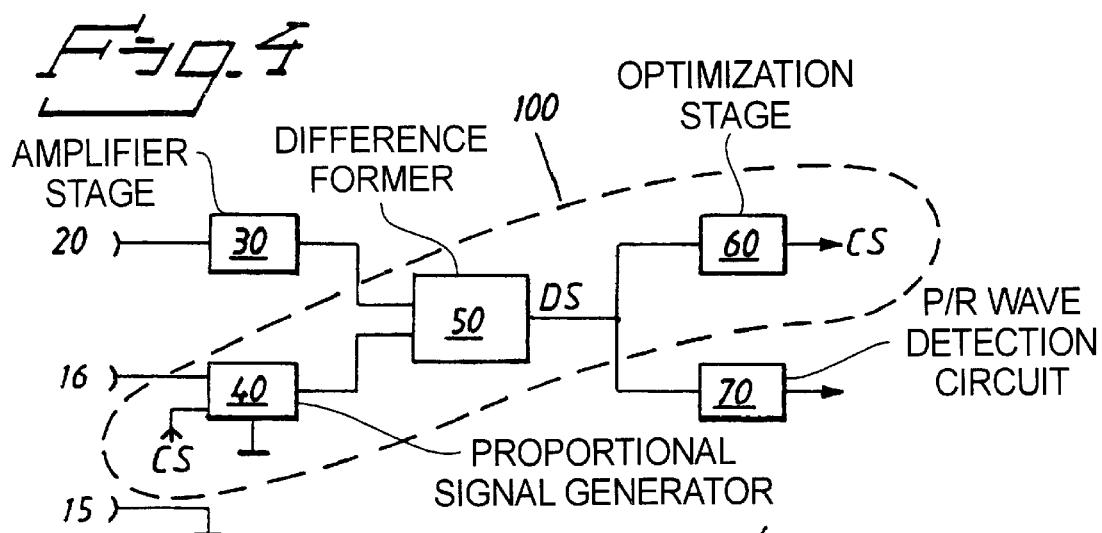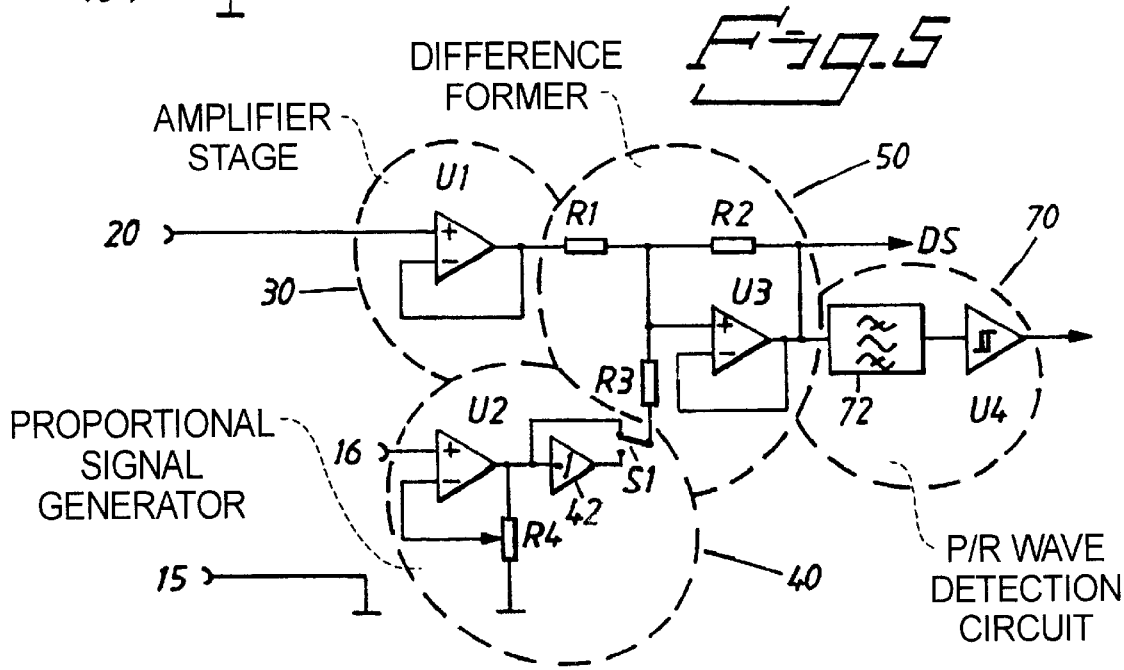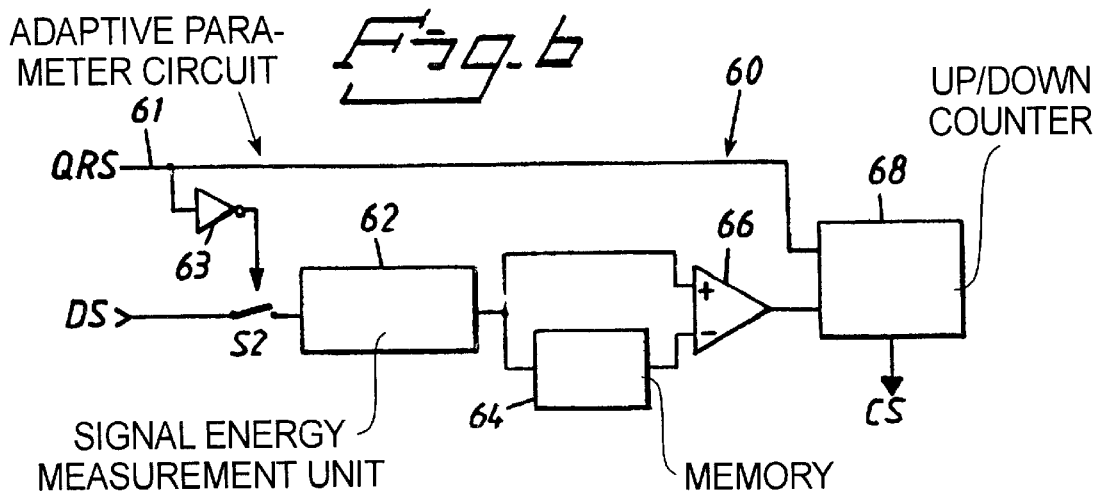

IMPLANTABLE CARDIAC STIMULATOR WITH CIRCUITRY FOR REMOVING NOISE IN SENSED ELECTRICAL SIGNALS

BACKGROUND OF THE INVENTION

1. Field of the Invention

The present invention relates to an implantable medical device for tissue stimulation such as heart pacemakers or defibrillators, and more particularly, to cardiac stimulating devices of the type having circuitry for removing noise in sensed electrical signals.

2. Description of the Prior Art

A pacemaker provides electrical stimulation pulses to the right atrium and/or the right ventricle of the heart in order to stimulate the muscle tissue to cause a contraction.

Demand pacemakers monitor the heart, through the same electrical leads through which the stimulation pulses are provided, in order to sense the occurrence of a P wave and /or R wave ("P/R wave"). If a P/R wave is sensed, then there is no need to deliver a stimulation pulse. In such an instance (when a P/R wave is sensed), the delivery of the stimulation pulse in a demand pacemaker is inhibited, thereby conserving the limited power of the pacemaker's battery, and further preventing irregular rhythms (contractions) of the heart muscle tissue that might otherwise result. Thus, a demand pacemaker provides stimulation pulses to the right atrium and/or right ventricle on demand, i.e. only when needed.

In dual chamber pacemakers there is not only an inhibiting function but also a trigged function. The sensing of a P wave inhibits the atrial stimulation. It furthermore triggers an AV interval, which stimulates the ventricle, if a ventricle activity has not been sensed before the AV interval runs out. If a ventricle activity is sensed, the ventricle stimulation is inhibited.

Similarly, automatic defibrillators provide a high energy stimulation pulse to cardiac tissue in an attempt to start contractions in a heart that has stopped. If the heart responds to such high energy defibrillation pulses and starts beating on its own, the need for defibrillation also operates in a demand mode, providing defibrillation pulses only when needed.

The ability of e.g. a demand pacemaker, dual chamber pacemaker or automatic defibrillator to properly perform its function of providing stimulation pulses on demand is critically dependent upon its ability to detect P/R waves. Unfortunately, many electrical signals may be present in a typical ECG signal (that signal sensed through the pacemaker or defibrillator leads) that do not represent valid P/R waves. Such signals are referred to as noise. Body movements may give rise to noise.

The stimulation of heart tissue and the detection of P/R waves is either provided by a unipolar lead or a bipolar lead. Unipolar stimulation and sensing is achieved between the tip electrode of the lead and the indifferent electrode of the tissue stimulating device, and bipolar stimulation and sensing is achieved between the tip electrode of the lead and the ring electrode of the tissue stimulating device. A bipolar lead may provide unipolar stimulation or sensing.

Thus, compared to a unipolar lead, a bipolar lead needs two insulated connections and wires for proper operation. The bipolar lead is therefore more sensitive to fatigue breakage, short-circuits and insulation defects. The ring electrode also renders the bipolar lead less flexible in the area of the ring electrode, and since the ring electrode is normally placed a few centimeters from the tip electrode where there is maximum bending of the lead, this results in fatigue breakage around the area of the ring electrode. Consequently, unipolar leads are for mechanical and quality reasons superior to bipolar leads.

However, in the bipolar system both the tip electrode and the ring electrode are placed inside the bean, and since the distance between the electrodes is small compared to the distance to muscles associated with body movements, the muscle signals affect the electrodes in much the same manner and consequently these muscle signals cancel each other. In the unipolar system the indifferent electrode is in close contact with muscles relating to body movements. The indifferent electrode is very likely to pick up signals from e.g. arm movements, and these signals can reach amplitudes far higher than the amplitude registered by the tip electrode as heart signal. Consequently, bipolar leads have a superior noise suppression and in particular of muscular interference.

One technique that can be used to reduce noise in a pacemaker is disclosed in U.S. Pat. No. 5,010,887 which relates to a noise discrimination circuit in implantable pacemakers. The noise discrimination circuit monitors the ECG signal to determine both the amplitude and duration of any signal pulses appearing thereon. If the amplitude of a given ECG signal pulse exceeds a prescribed threshold level for a prescribed duration, the pulse is considered to be a valid ECG signal.

U.S. Pat. No. 5,522,857 discloses another technique whereby a pacemaker comprises means for detecting the presence of noise by using two different escape intervals.

European Application 0 713 714 relates to an implantable medical device which comprises a correlator for producing a correlation function indicating the level of an EMIL (electromagnetic interference) component of an input heart signal that includes a heart signal component and an EMI component. The correlation function is monitored relative to a predetermined threshold to allow the device to operate in a normal manner as long as the intensity or level of the EMI component is such that it does not affect or interfere with the device operation. One or more remedial measures may be selected in the event the level of the EMI component exceeds a predetermined threshold.

SUMMARY OF THE INVENTION

It is an object of the present invention to provide a cardiac stimulator having a more reliable arrangement for reducing electrical noise signals originating from the human body without having to monitor the duration and/or amplitude of the sensed electrical signal.

The above object is achieved in accordance with the principles of the present invention in a medical device adapted for implantation in a human body for stimulating heart tissue having a housing which includes an indifferent electrode, an electrode lead connectable to the housing which has a tip electrode for sensing electrical signals originating within the heart tissue, and a noise sensing electrode connected to the housing for sensing electrical noise signals from the human body which originate outside of the heart tissue, the noise sensing electrode being electrically insulated from the indifferent electrode.

An advantage of providing a noise sensing electrode located outside the heart for sensing noise signals originating outside the heart is that there is no need for determining what is to be considered as noise, since everything sensed by the noise sensing electrode is considered to be noise.

DESCRIPTION OF THE DRAWINGS

FIG. 4 is a schematic block diagram of a noise cancellation circuit in accordance with the invention used in a heart pacemaker.

FIG. 5 is a schematic circuit diagram of a noise cancellation circuit in accordance with a preferred embodiment of the invention.

FIG. 6 is a schematic block diagram of an adaptive parameter circuit in accordance with a preferred embodiment of the invention.

DETAILED DESCRIPTION OF THE PREFERRED EMBODIMENTS OF THE INVENTION

Figure 1:
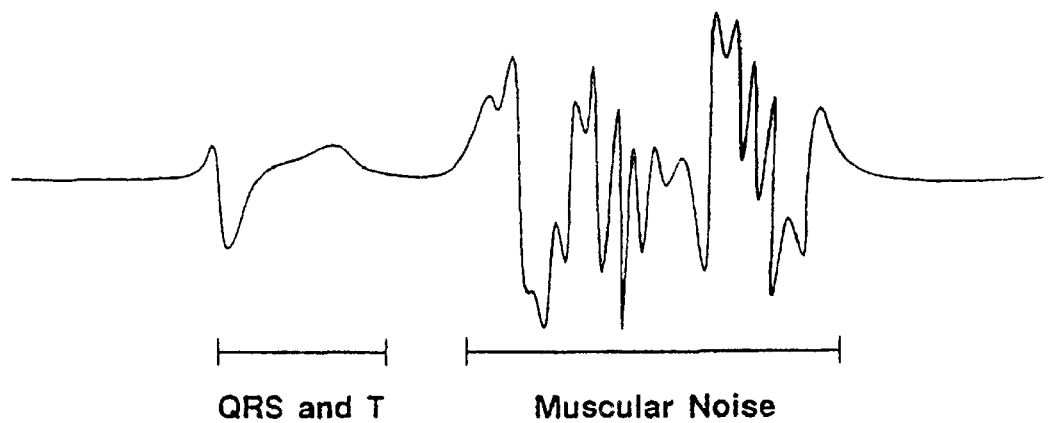
FIG. 1 is a schematic illustration of a sensed cardiac signal.

FIG. 1, illustrates a possible electrical signal in the heart sensed between the tip electrode 20 and the indifferent electrode 15. The electrical signal comprises not only a signal provided by the heart but also a noise signal provided by body movements, i.e. muscular noise. The heart signal and the noise signal are depicted next to each other for clarity. Usually these two signals are superimposed.

Figure 2:
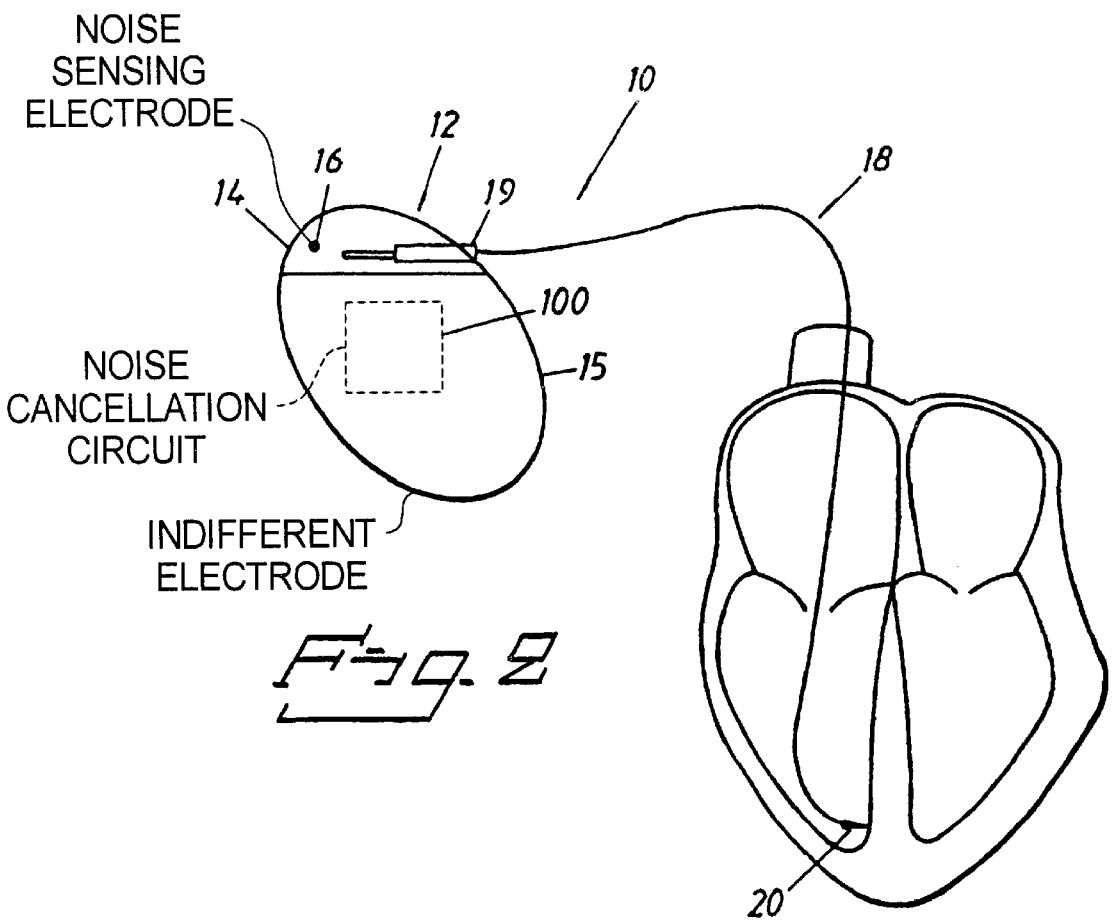
FIG. 2 is a schematic illustration of a heart pacemaker having a noise sensing electrode and a unipolar lead, in an embodiment of the invention.

FIG. 2, is a schematic drawing of a heart pacemaker 10 having a noise sensing electrode 16 and a unipolar lead 18 in accordance with an embodiment of the invention. The pacemaker 10 has a housing 12 which in FIG. 2 is composed of two parts, namely the case 15 and the header 14. The case 15 contains the pacemaker circuitry and the indifferent electrode 15. This configuration is well known in the art. A noise cancellation circuit 100 which will be more extensively described below is also contained in the case 15. The header 14 has a socket for receiving a connector 19 of the lead 18. The lead 18 is preferably a unipolar lead. However, a bipolar lead may also be used as long as the sensing of the heart activity is performed between the tip electrode of the lead and the indifferent electrode of the housing. The indifferent electrode is considered to be the common reference point when sensing heart activity between the tip electrode 20 and the indifferent electrode 15 and noise between the noise sensing electrode 16 and the indifferent electrode 15.

In FIG. 2 the noise sensing electrode 16 is placed on an additional lead 17 which is connected to the header 14. The length of the additional lead 17 may be so long that the electrode 16 still senses the signals for the same muscles which are sensed by the case 15. The distance between the noise sensing electrode 16 and the case 15 may be up to about 5 cm. The noise sensing electrode 16 is electrically connected to the noise cancellation circuit 100. Alternatively, the additional lead 17 may be connected to the case 15 for electrical connection of the noise sensing electrode 16 to the noise cancellation circuit 100, the prerequisite being that it is insulated from the case 15.

In a preferred embodiment the noise sensing electrode 16 is placed directly on the header 14, the header 14 being a convenient location for the noise sensing electrode 16, since the header is non-conducting and close to the indifferent electrode 15. No extra lead is needed and the 15 design becomes more resistant against breakage. However, the noise sensing electrode 16 may also be placed directly on the indifferent electrode 15, the prerequisite being that it is insulated from the indifferent electrode 15. This also applies to pacemakers without header, i.e. headerless pacemakers.

In yet another embodiment the tip electrode 20 includes the noise sensing electrode 16, e.g. the connector 19 may comprise the noise sensing electrode 16. In an alternative embodiment the noise sensing electrode 16 is located on the lead 18 between the connector 19 and the tip electrode 20, but at such a distance from the connector 19 that when the lead 18 is implanted the noise sensing electrode 16 is located outside the heart and predominantly senses electrical signals originating outside the heart. Also in this case it is a prerequisite that the noise sensing electrode 16 still senses the signals for the same muscles which are sensed by the case 15 and the distance between the noise sensing electrode 16 and the case 15 may be up to about 5 cm.

When using a headerless pacemaker, the noise sensing electrode 16 is connected to the case 15 as described above.

The housing 12 of the pacemaker 10 is implanted at a certain location in the body of a patient and has a certain orientation. However, neither the housing 12 nor the lead 18 are static. They may for example be moved from their implanted location and/or orientation by body movements.

Figure 3A:
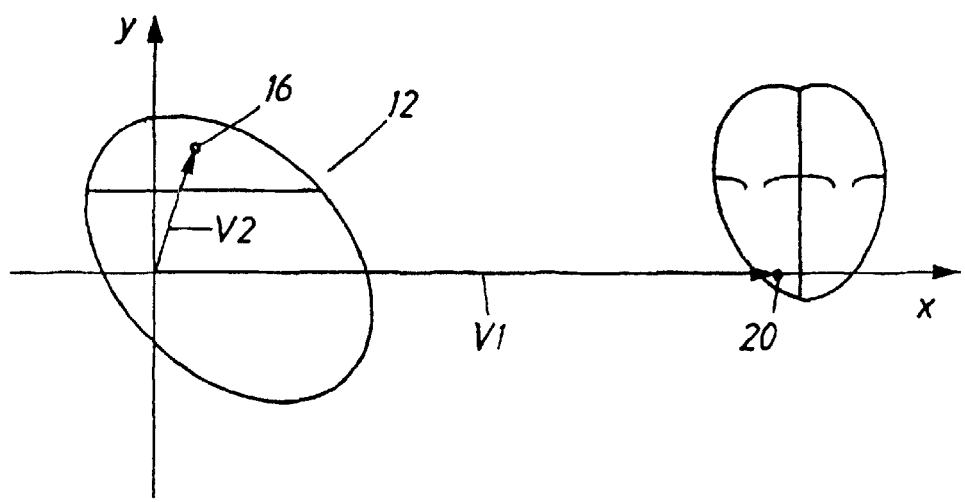
FIGS. 3A and 3B respective are schematic views of the vector relationship between the indifferent electrode, the tip electrode and the noise sensing electrode in the inventive heart pacemaker.
Figure 3B:
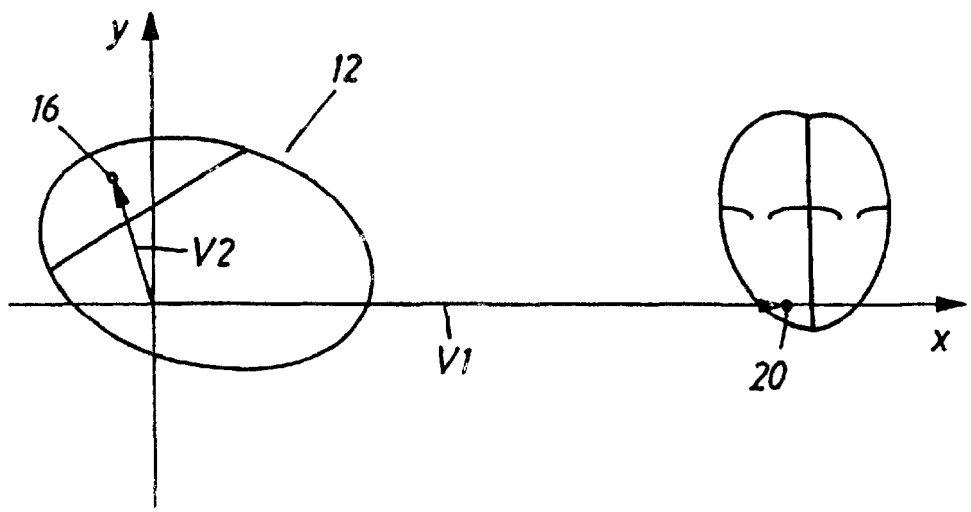

In FIGS. 3A and 3B are shown schematic views of the vector relationship between the indifferent electrode 15, the tip electrode 20 and the noise sensing electrode 16. Supposing that a coordinate system is generated comprising three points, each point represents an electrode, i.e. the indifferent electrode 15, the tip electrode 20 and the noise sensing electrode 16. The indifferent electrode 15 is placed in the origin and the tip electrode 20 is placed on the x-axis. The place of origin on the indifferent electrode 15 corresponds to the equivalent sensing point of the indifferent electrode 15. Usually the equivalent sensing point substantially corresponds to the center of gravity of the surface of the case 15. Depending on the position of the noise sensing electrode 16, it may be found in any of the four quadrants of the coordinate system.

In FIG. 3A, the noise sensing-electrode 16 is located on the header and is in the first quadrant. Hence, the first vector V1 is between the indifferent electrode 15/origin and the tip electrode 20, and the second vector V2 is between the indifferent electrode 15/origin and the noise sensing electrode 16. In this example, both vectors have the same polarity, since both the noise sensing electrode 16 and the tip electrode 20 are in the first quadrant.

However, starting from the example in FIG. 3A, it is possible that the housing 12 is moved in such a way that the polarity of the two vectors is no longer the same as can be seen in FIG. 3B.

In a preferred embodiment the noise cancellation circuit 100 comprises means 42,S1 for taking into consideration a difference in polarity of the two vectors. These means 42,S1 will be more extensively explained further down.

FIG. 4 is a schematic block diagram of a pacemaker circuit comprising a noise cancellation circuit 100. Two signals are inputted to the noise cancellation circuit 100, namely the by the amplifying means 30 amplified ECG signal sensed between the tip electrode 20 and the indifferent electrode 15 and the noise signal sensed between the noise sensing electrode 16 and the indifferent electrode 15. Consequently, the noise signal corresponds to the signal originating outside the heart tissue and the ECG signal corresponds to the signal originating within heart tissue, i.e. the ECG signal comprises both the pure heart signal and the noise signal.

The noise cancellation circuit 100 comprises means 40 for generating a signal proportional to the noise signal into which is inputted the noise signal. Thereafter the means 40 inputs the generated proportional signal to a means 50 for forming a differential signal DS. The differential signal forming means 50 also receives the amplified ECG signal, and forms the difference between the amplified ECG signal and the generated proportional noise signal. The differential signal DS is thereafter inputted into means 60 for optimising the noise cancellation, whereby a control signal CS is generated, which is input into the proportional signal generating means 40 for controlling the means 40. The control signal CS may either be generated by telemetry (not shown) or by an adaptive parameter circuit which will be described in connection with FIG. 6.

The differential signal DS, i.e. the sensed ECG signal free of noise, is also inputted into a detection unit 70 for determining if the ECG signal corresponds to a heart contraction as known in the art.

FIG. 5 is a schematic circuit diagram of a pacemaker circuit having a noise cancellation circuit 100 in accordance with a preferred embodiment. The sensed ECG signal is amplified by a linear amplifier U1 using negative feedback. The noise signal is also amplified by a linear amplifier U2. However, the gain of the linear amplifier U2 is adjustable by means of a potentiometer R4 for optimizing the noise cancellation. Thereafter, the polarity of the amplified noise signal is determined and adjusted by means of a switch S1 and a linear inverter 42. The switch S1 is controlled by the adaptive parameter circuit 60 which will be explained below. It is important that the polarity of the ECG signal and the noise signal is known, so that a correct noise cancellation may be performed. Normally, the polarity of the two signals is known at implantation, since the pacemaker is implanted into a patient's body having a certain orientation which orientation may be checked by the pacemaker expert. However, for different reasons, the position of the pacemaker may change, and the pacemaker should therefore preferably comprise means for adjusting the noise cancellation circuit to the change in polarity.

Thereafter, the signal proportional to the noise signal is cancelled from the amplified ECG signal using an adder 50 comprising an operational amplifier (Op-Amp) U3 using negative feedback, a resistor R1,R3 for each respective input and a resistor R2 between the output and input of the Op-Amp. Adders are well known in the art.

The output of the adder 50, which is the differential signal DS, is used on one hand for, optimising noise cancellation and on the other hand for determining a P/R wave. In FIG. 5 is shown how a P/R wave is determined by filtering 72, amplifying and asserting the differential signal D4 to a detection level U4.

Optimising the noise cancellation is either performed manually by a pacemaker technician using telemetry or automatically by using an adaptive parameter circuit 60. However, in both cases the gain of the noise signal amplifier U2 is changed by means of the potentiometer R4 until the optimal noise cancellation is obtained.

FIG. 6 is a schematic block diagram of an adaptive parameter circuit 60 in accordance with a preferred embodiment of the invention. The adaptive parameter circuit 60 comprises an up/down counter 68 which is clocked by the flank of a QRS detector 61. A control signal CS is outputted by the up/down counter 68, whereby the control signal CS comprises a most significant bit field and a data field. The most significant bit field comprises the bit informing if the control signal CS is positive or negative. The control signal CS controls the setting of the potentiometer R4, i.e. the potentiometer R4 is increased or decreased depending on the level of the differential signal DS compared to the preceding differential signal DS. Furthermore, the most significant bit of the control signal CS is used to control the switch S1.

A signal energy measurement unit 62 measures the signal energy of the differential signal DS. The signal energy is than compared in a comparator 66 with the signal energy of the preceding 64 differential signal DS and the result of the comparison is used for letting the up/down counter 68 count up or down. When the potentiometer R4 is adjusted for maximum elimination of noise, there will be a minimum in the signal energy level. A switch S2 is located before the signal energy measurement unit 62, the switch S2 being controlled by the QRS detector 61. Supposing that the switch S2 is always closed, this would mean that the signal energy level is determined by the energy of the total signal QRS+T+noise. If the QRS detector 61 controls the switch S2 to be opened during a time window prior to QRS+T, then the energy in the heart signal QRS+T will not influence the signal energy level and the adaptive parameter circuit 60 will control the setting of the potentiometer R4 and the polarity switch S1 such that a minimum of the noise signal is obtained.

One skilled in the art will appreciate that the present invention can be practiced by other than the described embodiments, which are presented for purposes of illustration, and the present invention is limited only by the claims which follow.

What is claimed is:

1. A medical device for implantation in a human body for stimulating heart tissue comprising a housing containing a noise cancellation circuit and an indifferent electrode at said housing connected to said noise cancellation circuit, an electrode lead mechanically connected to said housing and electrically connected to said noise cancellation circuit and comprising a tip electrode for sensing electrical signals, relative to said indifferent electrode, originating within said heart tissue, and said housing comprising a noise sensing electrode connected to said noise cancellation circuit for sensing electrical noise signals, relative to said indifferent electrode from the human body originating outside said heart tissue, said noise sensing electrode being electrically insulated from said indifferent electrode said noise cancellation circuit being supplied with the respective signals from said tip electrode and said noise sensing electrode, and cancelling said noise signals sensed by said noise sensing electrode from said electrical signals originating within the heart tissue sensed by said tip electrode, and said noise cancellation circuit comprising a proportional signal generator supplied with said signal from said noise sensing electrode for generating a signal proportional to the noise signal and a difference former which forms a difference signal as a difference between the electrical signal originating within the heart tissue and said proportional signal.

2. A device according to claim 1, wherein said housing comprises a header and wherein said noise sensing electrode is disposed at said header.

3. A device according to claim 1, wherein said proportional signal generator comprises an amplifier for amplifying said noise signal and components for adjusting a polarity of said noise signal.

4. A device according to claim 3, wherein said amplifier comprises a selectable proportional factor for varying said amplification.

5. A device according to claim 4, wherein said noise cancellation circuit comprises an optimization stage for optimizing said noise cancellation, said optimization stage comprising a comparator for comparing said difference signal to a precedingly formed difference signal, and a selector for selecting said proportional factor as a result of said comparison.

6. A device according to claim 5, wherein said selector comprises a step counter (68).

7. A device according to claim 4, wherein said noise cancellation circuit comprises an optimization stage for optimizing said noise cancellation, said optimization stage comprising a telemetry unit for making the difference signal available for comparing said difference signal to a precedingly formed difference signal and a selector for selecting said proportional factor as a result of said comparison by said telemetry unit.

\* \* \* \* \*